US004001557B2

United States Statutory Invention Registration [19]

[11] Reg. Number: H1557

Joubert et al.

[45] Published: Jul. 2, 1996

[54] SWALLOWING REHABILITATION

[76] Inventors: Carl A. Joubert, 8538 Bristlecone, San Antonio, Tex. 78240; Kali K. Fessenden, WHMC/SGHAE, Lackland AFB, Tex. 78236-5300; Karen V. Myers, 835 Firefly Dr., San Antonio, Tex. 78216

[21] Appl. No.: 187,374

[22] Filed: Jan. 27, 1994

Related U.S. Application Data

[62] Division of Ser. No. 907,910, Jul. 2, 1992.

[51] Int. Cl.[6] ..... A61B 5/103

[52] U.S. Cl. ..... 128/782; 128/905

[58] Field of Search ..... 128/716, 719, 128/725, 727, 728, 748, 774, 777, 782, 905, 200.24, 897, 898; 482/13; 73/23.3, 700, 756; 340/573, 626

[56] References Cited

U.S. PATENT DOCUMENTS

| | | | |
|---|---|---|---|
| 3,509,767 | 5/1970 | Greer | 128/716 |
| 3,656,474 | 4/1972 | Gentry et al. | 128/716 |
| 3,895,533 | 7/1975 | Steier | 128/727 |
| 4,198,969 | 4/1980 | Virag | 128/200.21 |
| 4,317,107 | 2/1982 | Trattner | 340/626 |
| 4,324,260 | 4/1982 | Puderbaugh | 128/728 |
| 4,495,944 | 1/1985 | Brisson | 128/725 |
| 4,635,647 | 1/1987 | Choksi | 128/728 |
| 4,787,627 | 11/1988 | Daubenspeck | 272/99 |
| 4,860,766 | 8/1989 | Sackner | 128/748 |
| 4,981,295 | 1/1991 | Belman et al. | 272/99 |
| 5,134,886 | 8/1992 | Ball | 73/718 |

OTHER PUBLICATIONS

Renault, F., et al. "Electromyographie faciale, . . . physiopathologie" *Neurophysiol. Clin* 1992, Jun., 22, pp. 249–260.

Heimlich, Henry J. "Rehabilitation of Swallowing After Stroke" *Rhinology & Laryngology,* 1983, 92, pp. 357–359.

Silverman, Ellen et al. "Dysphyagia: An Evaluation and Treatment Program" *Journal of Occupational Therapy,* Jun. 1979, vol. 33, No. 6, pp. 382–391.

Reddy, N. P. et al. "Noninvasive acceleration . . . swallowing" *Journal of Biomedical Engineering,* Sep. 1991, 13(5), pp. 379–383.

*Primary Examiner*—Harold J. Tudor
*Assistant Examiner*—Christopher K. Montgomery
*Attorney, Agent, or Firm*—Gerald B. Hollins; Thomas L. Kundert

[57] ABSTRACT

An arrangement for rewarding tongue-retraction exercise therapy performed by swallowing-impaired surgical and disease patients is disclosed. The achieved therapy includes execution of an oral sucking act (as opposed to lung originated suction) in combination with provision of a patient communicated incentive feedback signal measurement of the sucking act pressures —pressures below atmospheric pressure. The patient communication includes a visual bar graph related display and in the disclosed apparatus is provided with a plurality of four scale ranges in order to accommodate patients of varying swallowing act impairment. The achieved base of tongue strengthening exercise has been found to enable swallowing recovery in weeks in lieu of the expected months (or never) that is normally seen in severely impaired surgical or disease patients. A discussion of the swallowing act and its impairment behavior is included.

23 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SWALLOWING REHABILITATION

RIGHTS OF THE GOVERNMENT

The invention described herein may be manufactured and used by or for the Government of the United States for all governmental purposes without the payment of any royalty.

This application is a division of application Ser. No. 07/907,910, filed 02 Jul. 1992.

BACKGROUND OF THE INVENTION

This invention relates to the fields of medical patient physical therapy, the apparatus used in such therapy, and to medical measuring apparatus.

Several classes of medical patients are known to incur difficulty in performing the swallowing function used routinely by normal persons in eating and drinking. Particularly, surgical patients who have undergone cancer-related head and neck surgical procedures are known to experience this swallowing difficulty or dysphagia in an extreme form. Surgeries such as tonsil and soft palate resection with primary tongue closure, partial glossectomy, extended supraglottic laryngectomy with base of tongue resection, and partial and complete pharyngectomy are examples of the life-saving but drastic procedures that are found to initiate great difficulty in recovering the ability to perform a normal swallowing function.

Frequently, patients of this type, especially those receiving post-operative radiation treatment, require a prolonged period of hospitalization, tube feeding, and slow progress —progress extending over many months of hospitalization, in order to achieve even a limited degree of normal swallowing ability. Unfortunately, experience has also shown that many of these patients can never return to normal eating and drinking and require lifelong tube feeding because of a permanently impaired swallowing reflex.

In addition to a need for assisting patients of this type in the recovery of swallowing ability, patients in these surgical categories who are fortunate enough to retain the vocal cord and voice box structures in the area of surgery are often nevertheless faced with an inability to use these structually unaffected components as a result of nerve and muscle impairment that is collateral to the surgical procedure.

It also is often found that patients with non-surgical neurological and neuromuscular disorders—such as head injuries, cerebro-vascular accidents or strokes, amyo-tropic lateral sclerosis (ALS) or Lou Gehrig's disease, and other disorders can be faced with swallowing and speaking impairments of significant proportion.

A particularly troublesome effect of all of these surgical and disease-related dysphagia disorders arises from an inability of patients with such conditions to escape aspiration of food into their larynx, trachea, or windpipe during the act of swallowing. This condition results in considerable discomfort to the patient and presents the repeated threat of choking, airway distress, and possibly pneumonia. It is, in fact, the food and liquid aspiration threat which usually causes the long-term or permanent loss of normal eating and drinking in these patients.

It is now known that many of these surgical and disease patients can respond favorably to a regimen of dysphagia therapy that is directed to strengthening the base of tongue (BOT) region of the throat and neck. Such patients can therefore frequently be significantly assisted by persistent therapy routines which recondition and strengthen the retained muscle and nerve functions attending the swallow. Such strengthening of the BOT area increases the patient accomplished pulsion force in the pharynx and this improvement helps drive the bolus or liquid or chewed food mass through the pharynx in an aspiration-free proper swallowing sequence.

The patent art includes several examples of patient responsive or patient energized apparatus that are useful in the therapy field. Included in this patent art is the volumetric spirometer of George Puderbaugh disclosed in U.S. Pat. No. 4,324,260; the incentive spirometer employing a bellows airflow sensor of Philip Choksi as disclosed in U.S. Pat. No. 4,635,647; and the respiratory training using feedback of Michael Bellman in U.S. Pat. No. 4,981,295. Although each of these patents discloses a measuring system capable of providing feedback to a using patient, it is notable that all of these patents involve measuring systems which are intended for positive pressure use with the lungs.

Also included in the patent art is the suction operated nebulizer of Robert A. Varag, as disclosed in U.S. Pat. No. 4,198,969. Although the Varag apparatus does operate in response to suction or negative pressure, it is notable that this pressure also originates in the patient's lungs and that a primary purpose of the invention is to supply liquid into a stream of gas and deliver this mixture into the patient's lungs.

None of these prior patent examples therefore considers the problem addressed by the present invention, including the incentive rewarding of a patient while performing a therapy related act of oral sucking.

SUMMARY OF THE INVENTION

In the present invention, an oral sucking act therapy exercise for a dysphagic patient is accompanied by a feedback incentive display of accomplished results. Such feedback is provided by way of measuring the below atmospheric or negative pressure achieved by the patient during the sucking act and by displaying an easily comprehended indication of this pressure to the patient. The accommodation of improving capabilities in the patient is included.

It is an object of the invention therefore, to provide a rewarded exercise arrangement for assisting swallowing disorder patients.

It is another object of the invention to provide a base of tongue function measuring and effort rewarding system for swallowing disorder patients.

It is another object of the invention to provide an incentive feedback apparatus for a swallowing disorder patient.

It is another object of the invention to provide a sucking force measurement apparatus.

It is another object of the invention to provide a method for encouraging base of tongue exercise performance by dysphagia patients.

It is another object of the invention to provide a base of tongue exercise system which can accommodate differing and increasing levels of exercise performance.

It is another object of the invention to provide a real-time exercise feedback apparatus for dysphagia patients.

It is another object of the invention to provide exercise feedback for a dysphagia patient in a convenient and easily comprehended graphic form.

It is another object of the invention to provide a sucking act exercise feedback incentive apparatus that is small in physical size and easily portable in nature.

It is another object of the invention to provide a dysphagia patient feedback incentive apparatus that may be conveniently shared by a number of patients or alternately, may be assigned to use by a single patient.

It is another object of the invention to provide a dysphagia patient feedback apparatus that is low in cost and reliable in operation.

Additional objects and features of the invention will be understood from the following description and claims.

These and other objects of the invention are achieved by the method for improving the swallow function of a surgical neurological disease, neuromuscular disease or the like dysphagia patient comprising the steps of: tasking the patient to repeatedly execute the oral sucking act in a regimen of dysphagia therapy; the sucking act including reconditioning exercising usage of tongue, base of tongue, pharynx and related anatomical parts by the patient; generating an electrical signal representing a mouth cavity suction pressure, below atmospheric pressure, achieved by said patient during said sucking act; and rewarding and stimulating said patient into repeated strengthened repetition performance of said sucking act dysphagia therapy; said rewarding and stimulating comprising displaying a graphic representation of said suction pressure electrical signal as a results feedback incentive to said patient.

DETAILED DESCRIPTION

Figure 1A:
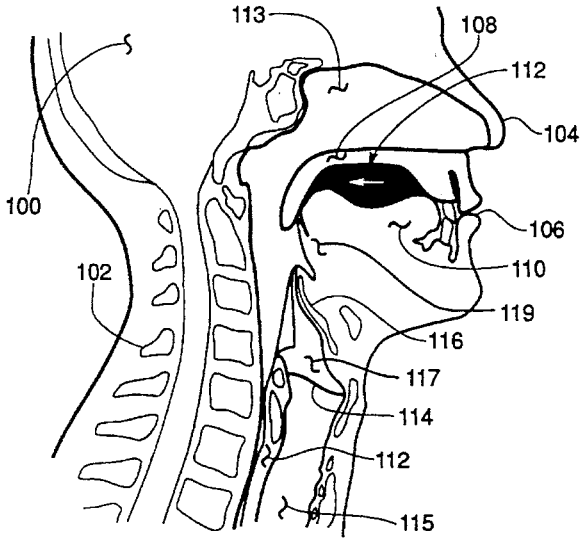
Fig. 1A PRIOR ART
FIG. 1, which includes the views of FIG. 1A, FIG. 1B, FIG. 1C, FIG. 1D and FIG. 1E, show a lateral representation of the normal human swallowing function.
Figure 1B:
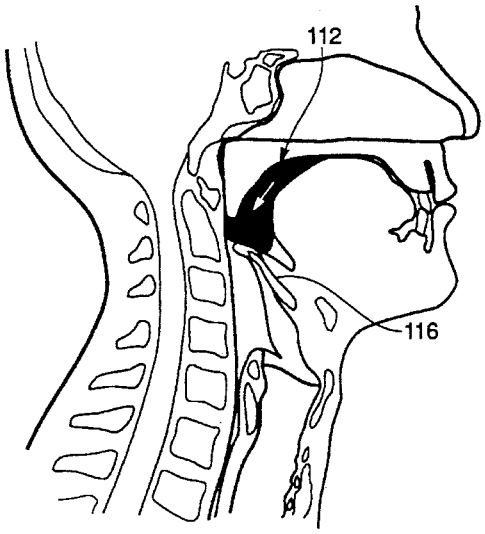

The five parts of FIG. 1 in the drawings shows a sequential view of salient steps in the normal human swallowing sequence. The FIG. 1 views and portions of the following text related thereto are based on a description appearing in the text *Evaluation. and Treatment Of Swallowing Disorders,* Logemann, College Hill Press, 1983, and are used herein through the courtesy of Pro Ed Incorporated of Austin Tex. 78758, the present owners of the Logemann text copyright.

The FIG. 1 views are in the form of lateral semi cross-sections. In the FIG. 1A first of these views, there is represented the skull 100, the spinal vertebrae 102, the nose 104, the mouth 106, and the soft palate 108, of the human head and throat region. Additionally shown in the FIG. 1A view are the trachea or windpipe 115, the cervical esophagus 112, the nasal or sinus cavity 113, the vocal cords 114, the epiglottis 116 and the larynx 117.

The FIG. 1A, 1B, 1C, 1D, and 1E sequence of views shows the propulsion of bolus 112, a mass of chewed food, during a swallowing sequence. In the FIG. 1A view, the tongue 110 has initiated the swallow reflex and has confined the bolus 112 between the tongue 110 and the soft palate 108. In the FIG. 1B view, the pharyngial swallow reflex has been initiated by a forcing of the bolus into the rear of the mouth where pressure receptors in the walls of the oral pharynx are stimulated. These pressure receptors communicate information to the swallowing center in the brain which coordinates a sequence of events by way of communicating impulses to muscles in the oral pharynx, larynx, epiglottis, and respiratory muscles. The esophagus 116 is shown in the FIG. 1B view to have commenced its closure movement.

Figure 1C:
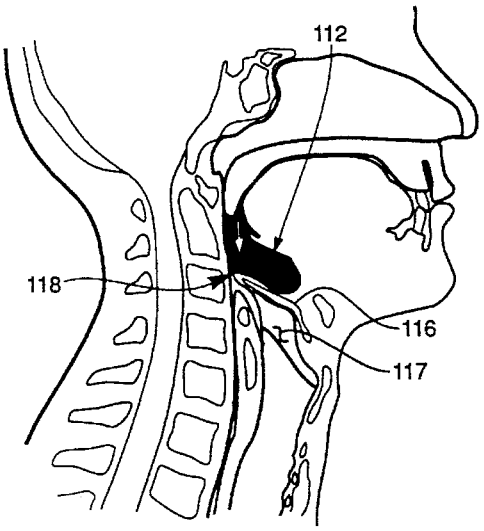
Figure 1D:
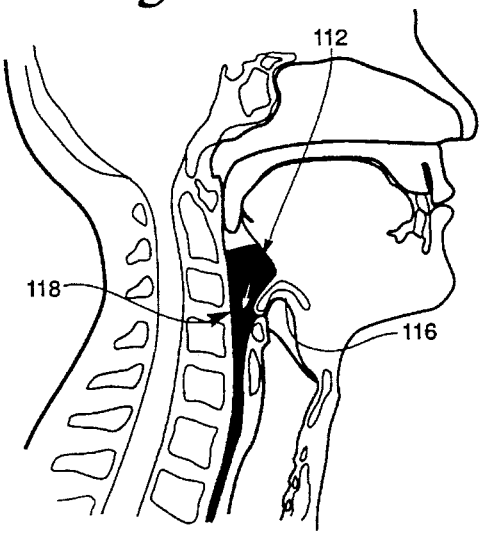
Figure 1E:
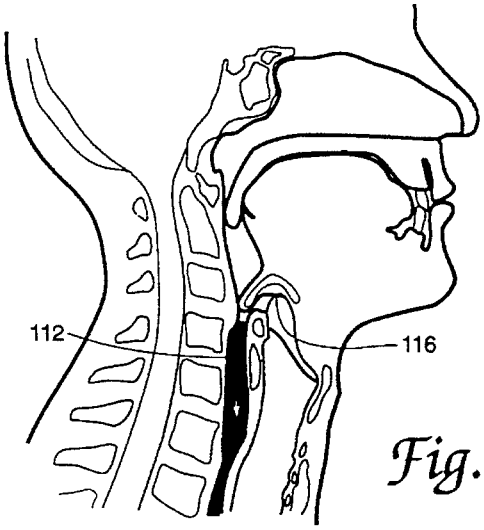

In the FIG. 1C view, the bolus 112 is passing into the oral pharynx region 118 and the epiglottis 116 is approaching the state of closing off the larynx wherein resides the vocal cords 114. In the view of FIG. 1D, the bolus 112 is passing through the circopharyngeal sphincter into the cervical esophagus. Significantly, the epiglottis 116 is in a fully closed state wherein the larynx and the trachea are completely closed off and fully isolated from the bolus 112 in the view of FIG. 1D. In the view of FIG. 1E, the pharyngeal stage of the swallow is complete, the entire bolus 112 is now received in the cervical esophagus 112 and the epiglottis 116 is commencing an opening movement.

A number of important but less noticeable events are also included in the FIG. 1 normal swallow sequence. These events include an elevation of the larynx 117 which may be observed by comparing its position in FIGS. 1A and 1C, for example, and a retraction of the base of tongue (BOT) region back toward the posterior pharyngeal wall as may be appreciated by comparing FIGS. 1A and 1D, for example. Movement of the pharyngeal wall itself is also observed in X-ray or video fluoroscopic studies of the swallow.

Even in this simplified description of human swallowing, it can be appreciated that many possible interruptions to the swallowing sequence can provide considerable difficulty for a surgical or neurological disease patient. It is particularly notable, for example, that failure to achieve complete inversion and closure of the epiglottis as shown in FIG. 1D provides an unobstructed path for portions of the bolus to enter the larynx 117 and trachea 115 (i.e., for food to go down the windpipe and produce choking). Interruptions such as poor communication of the "to" and "from" signals to the brain, as described in connection with FIG. 1B, or inadequate base of tongue region 119 retraction or loss of good muscle control over the opening and closing of the epiglottis 116 are also often observed in clinical practice. Poor coordination of the epiglottis opening and closing, as often occurs in surgical patients and in neurological disease patients, and the retention of status material, therefore, is frequently observed and can lead to extreme discomfort and danger in the form of aspiration, airway distress, and possible pneumonia in a patient.

Dysphagia therapy has been found to be of significant assistance in returning the above-described swallowing sequence to many patients of the presently addressed class. This return appears in fact to occur in a manner akin to the perhaps better-known use of physical therapy for returning physical function and strength to the peripheral limbs of a patient. For some time, however, there has been debate and question in the medical art as to an effective way for accomplishing therapy in the case of swallowing disorders.

Therefore, although medical patients with swallowing difficulties have been known for quite some time, it is a relatively recent evolution to appreciate that these patients too can be assisted with physical therapy exercise. In fact, there has been a recently growing awareness in the speech therapy profession that some form of tongue base retraction exercise or base of tongue strengthening exercise is desirable for these patients. The earliest known attempts in this direction have included attempts to use pronunciation of the "K" sound as in the word "kick" or "key" as a speech therapy exercise.

We have found, however, that patient execution of the oral sucking act, that is, creating a negative pressure in the mouth cavity by a backward and downward motion of the tongue is, in fact, an effective speech therapy exercise for the swallow related base of tongue region. As may be verified by personal experimentation, this downward and backward motion is easily performed in the presence of a sealed tongue to soft palate condition at the rear of the mouth and in fact, does not interrupt normal breathing and lung functions. Indeed, with persistent devotion to an exercise of this nature, surprising recoveries in dysphagic or swallowing disorder patients can be achieved. In certain instances, for example, an expected seven-month recovery time for dysphagic surgical patients has been reduced to a few weeks with the aid of the present invention combination.

Since this base of tongue strengthening exercise is in fact in the nature of an isometric exercise and therefore without the production of tangible or sensory stimulating reward to the patient for his/her expended effort, there has been a notable tendency for patients to become discouraged, tired, and disinterested in the execution of such exercises. This phenomenon is not unknown in other therapy programs. It is an aspect of the present invention, therefore, to provide an incentive feedback or results achieved indication which may be communicated to a patient performing the oral sucking act therapy. In fact, this feedback may take the form of a visual signal as is preferred or may be in the form of other sensory input stimulations such as an audio signal or a tactile signal, if needed. This feedback in effect closes the loop on the BOT dysphagia therapy exercise.

This loop closing not only acts as a reward—or a measure of accomplishment for the patient but also, especially in the initial stages of the therapy program, is a reassurance to the patient that the correct exercise motion is being performed. In this regard, if a patient is achieving measurable and increasing magnitudes of oral suction pressure then in fact, the base of tongue region of the patient's throat is participating in the desired therapy exercise. This reassurance of performing the correct movements and force exertions is especially important in initial stages of the therapy program and to patients having such nerve impairment that normal perception of these force exertions is altered.

Repeated and sustained performance of the oral sucking act (as is somewhat instinctive in newborn infants and indeed in newborn of most vertebrate species) is therefore an effective physical therapy mechanism for the anatomical elements used in the swallowing act. The oral sucking act, as is of interest in the present context, is to be distinguished from a sucking or vacuum or negative pressure condition having its origin in the lungs. It is, of course, also possible for humans to create a vacuum condition with lung-originated suction —such suction is often used, for example, when a person siphons liquid through a length of tubing. The desired oral sucking act is in fact usually capable of creating greater negative pressures (i.e. pressures more below atmospheric) without discomfort than is lung originated suction.

The oral sucking act, as is of interest for the present physical therapy purposes, is executed with the tongue 110 much in the position shown in FIG. 1A. In this position, the rear of the tongue 113, that is the BOT region 119, is sealed against the soft palate 108. In contrast with the muscle movement described for FIG. 1A during an oral sucking act, the tongue is urged in a downward and rearward or posterior direction so that a somewhat surprisingly large negative pressure or vacuum is generated in the region previously occupied by the bolus 112 in FIG. 1A view. Closure of the tongue at the front of the soft palate 108 is optional during the oral sucking act. This may be demonstrated by executing an oral sucking act with the teeth open—while simultaneously appreciating the possibility of drawing the sides of the mouth into the space between the open teeth with the generated oral suction force.

The distinction between an oral suction act and a lung originated suction event may also be appreciated by the reader executing an oral sucking act and retaining the negative pressure condition in the mouth while simultaneously continuing breathing with the lungs. Clearly in this latter demonstration a sealing of the tongue, particularly the base of tongue region 119 of interest in the present therapy, against the rear portions of the soft palate 112 as shown in FIG. 1A is occurring.

Dysphagia therapy to this base of tongue region is therefore found to be an effective treatment for many patients affected by the surgical or disease disorders described above. Even though the execution of an oral sucking act is an effective form of this therapy, there exists as is true in most other forms of therapy, a need for an incentive or reward system including a progress measuring arrangement, to motivate these dysphagic patients through an extended period of therapy. To a patient who is in a weakened, discouraged and painful condition already, the presence of an effective incentive and reward arrangement can be of great significance and in fact, can strongly influence the time of recovery for the patient.

In actual cases, for example, prior to use of the apparatus described herein, one typical partial glossectomy patient's recovery time to a reasonable state of normal swallowing, required a period of three weeks and a second total pharyngectomy procedure patient's recovery time required a period of five weeks. With early experimental and perfecting uses of the therapy and the apparatus described in FIGS. 2 and 3 herein, a third patient having a similar degree of surgical involvement to the first patient above, accomplished the same degree of recovery in a period of two weeks and a fourth patient having a degree of involvement differing to the second patient above accomplished a recovery in four weeks. The concepts of the present invention have also been found to be effective with supraglottic laryngectomy patients during post-operative radiation treatment to maintain swallowing function without aspiration.

Figure 2:
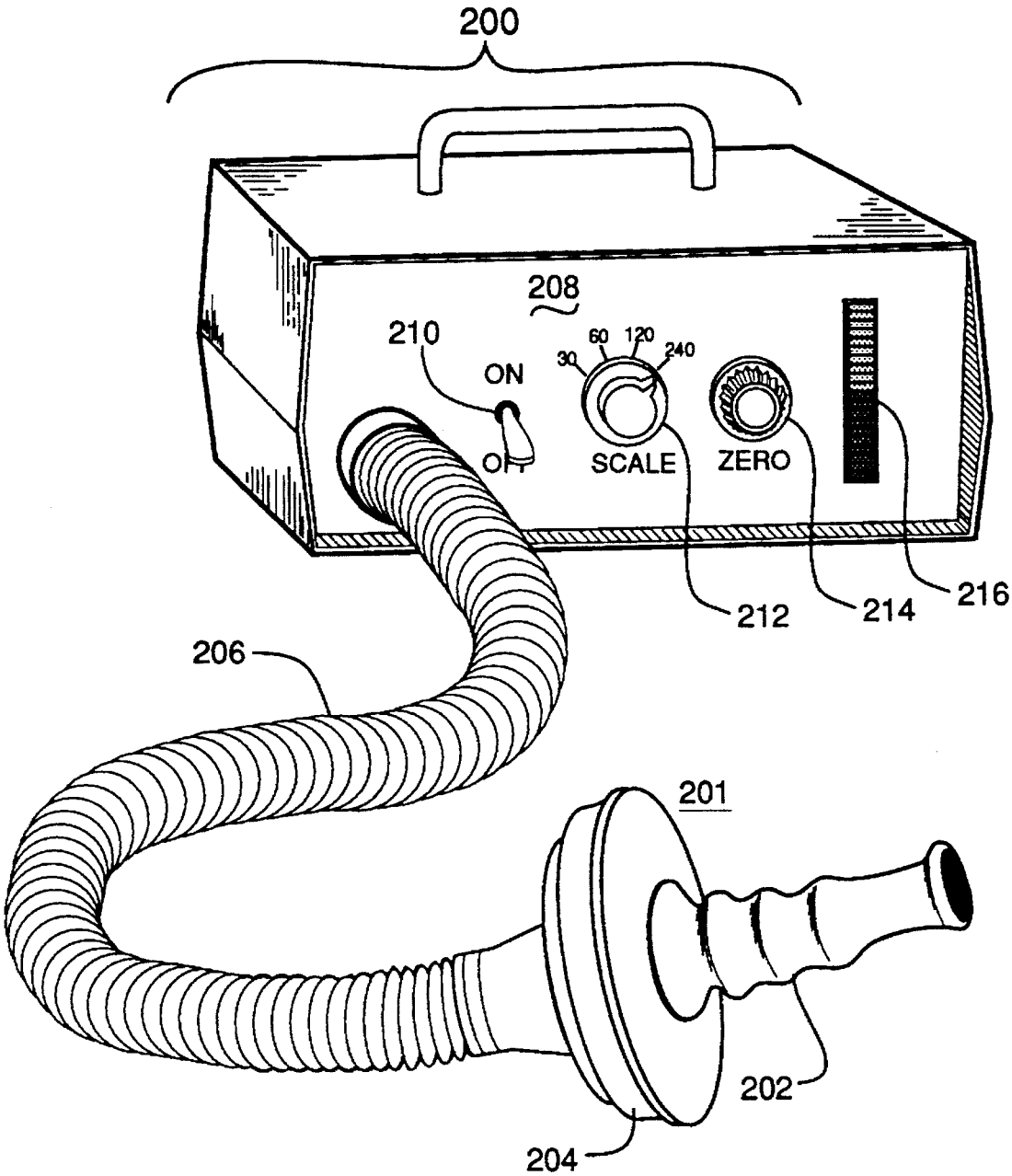
FIG. 2 shows an overall view of an oral suction act incentive feedback apparatus.

FIG. 2 in the drawings shows an overall perspective view of an apparatus which may be used in this providing of a reward or incentive to dysphagic patients. The FIG. 2 apparatus may also be used as a tool in evaluating a patient's progress and needs and as an assistance to the speech therapist in formulating a program to fit specific patient needs. This FIG. 2 apparatus accomplishes a measurement and display of the suction levels or negative pressures, or degree of vacuum achieved by the dysphagic patient during execution of an oral sucking act.

The FIG. 2 apparatus 200 is comprised of a patient interface assembly 201, which includes the paper tube mouthpiece element 202 and an air filter unit 204. Communicating between the patient interface assembly 201 and the electronics assembly 208 is a short length of flexible tubing 206 of a type described in Table 1 located at the close of this description. The patient interface assembly 201 as well as the vacuum transducer element received in the electronics assembly 208 may be of types commonly used in the medical measurement art, specific examples of these elements being identified in Table 1.

The electronics assembly 208 in FIG. 2 is shown to include a power switch 210, a pressure range selection or scale switch 212, a zero output adjustment potentiometer 214, and a graphic display assembly, preferably of the linear array light emitting diode type as shown at 216. As indicated in Table 1, the FIG. 2 apparatus can be small in physical size and weight, a size of 8×6×4 inches and a weight of 2.5 pounds is a feasible combination.

Use of the FIG. 2 apparatus 200 by a dysphagic patient involves placement of the mouthpiece element 202 in a sealed relationship with the patient's lips during execution of an oral sucking act. Measurement of the achieved level of suction or below atmospheric pressure is accomplished by way of a pressure to electrical signal transducer located in the apparatus 208 and communicated to the patient by way of graphic display 216. The pressure range selection switch 212 is placed in one of the 30, 60, 120 or 240 millimeters of mercury negative pressure full scale ranges during this patient use of the apparatus 200. Selection of the 30, 60, 120 or 240 millimeters full scale range can of course, be accomplished in response to the abilities and the stage of recovery of the patient using the apparatus 200. Persons with normal swallowing capability can readily provide oral sucking act negative pressures appropriate for the zero to 240 millimeters of mercury pressure range, for example. On the other hand, patients with severely impaired swallowing capability are found to be capable of oral sucking act pressures falling in the zero to 30 millimeters of mercury scale shown for the switch 212.

The on-off switch 210 of the electronics assembly 208 is of course used to apply power from the normal wall outlet or self-contained batteries to the internal circuitry of the electronic assembly 208. The range zero adjustment or zero output adjustment potentiometer 214 in FIG. 2 is used to accommodate component drift and variations in atmospheric pressure so that the indication from the graphic display 216 commences at the lowest or zero pressure indicating element. Additional details of the electronics assembly 208 are shown in the schematic diagram of FIG. 3 herein.

Figure 3:
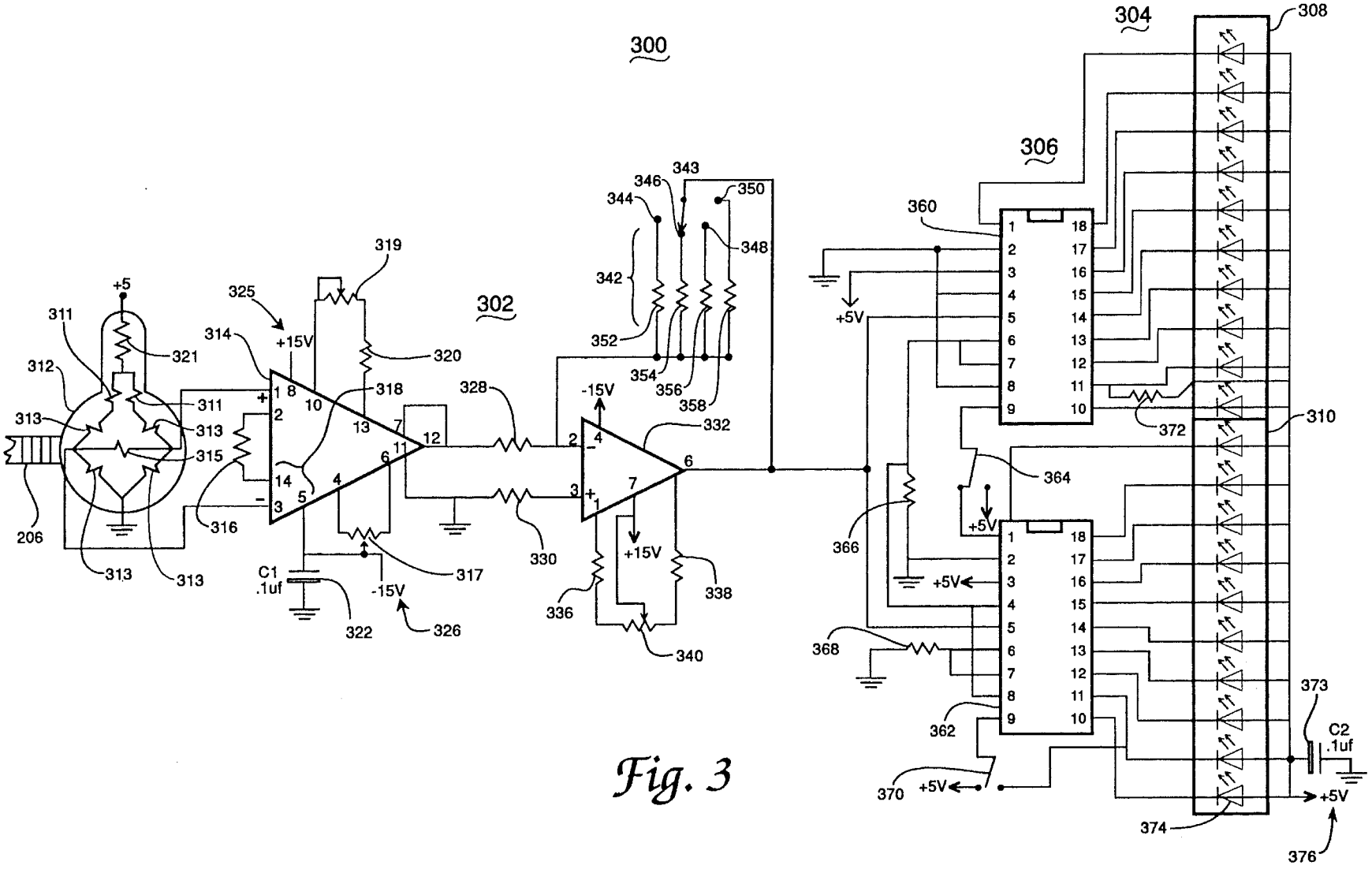
FIG. 3 shows an electrical schematic of the FIG. 2 apparatus.

In FIG. 3, there is shown an electrical schematic diagram of the circuitry used in the preferred embodiment of the electronics assembly 208. The FIG. 3 circuitry 300 includes a negative pressure to electrical signal transducer 312, an amplifier circuit portion 302, and a display system 304. The transducer 312 in the circuitry 300 is connected with patient communicating flexible tubing 206 which was shown in the FIG. 2 drawing and as is represented at the left-hand edge of FIG. 3. The electrical output signal from the transducer 312 is applied to the first operational amplifier 314 of the FIG. 3 circuit in the manner of an instrumentation amplifier. The amplifier 314 provides a negative polarity output signal at the output terminal 12. The numbers in and around the amplifier 314, the numbers indicated at 318 are pin identification numbers used with the type AD 521 embodiment of the amplifier 314 described in Table 1 herein.

Information from the manufacturer's data sheet may be used to fully comprehend the function of the circuit elements connecting with the amplifier 314, however, in general the potentiometer 319 and the fixed resistor 320 serve to adjust the output signal at pin 12 of the amplifier 314 to provide an output signal from the display drivers 360 and 362 that is just below the ignition threshold for the lowest order light emitting diode element 374 in the display segments 308 and 310. The potentiometer 319 is in fact, the electrical representation of the zero control shown at 214 in the FIG. 2 apparatus 200. Electrical values for the potentiometer 319, the resistor 320 and the other electrical components of the apparatus 300 are disclosed in Table 1 herein.

As shown in FIG. 3 of the drawings, the transducer 312 may be embodied in the form of an electrical bridge circuit, especially an electrical bridge circuit wherein the arms 313 of the bridge are changed in electrical resistance by the suction signal communicated by the flexible tubing 206. The transducer identified in Table 1 herein is a flow-through device originally in fact intended for blood pressure measurement use. This transducer is fabricated on a 0.011 inch square silicon chip which includes a pressure responsive diaphragm so that a differential output signal is obtained from the four arms of the electrical bridge circuit in the disrupted balance manner known in the electrical art.

The two resistors 311 and the resistor 315 in the transducer 312 are used by the manufacturer in adjusting the zero pressure output signal and the sensitivity or span of individual transducers by a laser trimming operation. The resistor 321 aids in providing transducer thermal stability. The electrical bridge circuit is energized from the +5 volt power supply, as is shown in FIG. 3, in instances where the transducer is comprised of an electrical bridge circuit arrangement. Clearly, other types of transducers including self-generating transducers of the magnetic or crystal type could be used with the invention with suitable changes in the FIG. 3 electrical circuitry.

It is significant to note that the transducer used in the FIG. 2 and FIG. 3 apparatus is required to respond to suction pressures or pressures less than atmospheric. The preferred Cobe Laboratories Inc. (Lakewood Colo. 80215) disposable transducer is specified for use in the −50 to +300 mmHg pressure range but is found to prform well in the −240 mmHg range of the FIGS. 2 and 3 apparatus. Transducers of a suitable type are also available as an Isotc disposable transducer from Healthdyne Cardiovascular Inc., 2253 Northwest Parkway, Marietta Ga. 30067.

The flexible tubing 206 is preferably provided with a cardboard mouthpiece and a personal filter element for use by each patient in order that sterile conditions between multiple patient users of the FIG. 2 apparatus can be maintained. The paper tube and filter elements of the FIG. 2 assembly 201 may be varied in size according to the age and physical size of the patient using the FIG. 2 apparatus. A possible variation of the FIG. 2 apparatus contemplated by the invention includes locating the transducer 312 at a point physically close to the patient's mouth in order to reduce the volume of air the patient must displace with the oral sucking act before achieving his/her maximum effort suction. Lung suction can also be used with the larger volume of the tubing 206 to aid this evacuation process. The transducer 312, the tubing 206 and indeed the entire assembly 201 are preferably arranged to be of a pneumatically closed or constant volume nature in any embodiment of the invention; this is in order that the limited air displacement of an oral sucking act be sufficient to achieve the desired negative pressures at the transducer 312.

The resistor 316 in the input circuit of the amplifier 314 of FIG. 3 serves as a gain selection device, and the potentiometer 317 serves as a zero adjustment for the amplifier 314. The capacitor 322 serves as a high frequency bypass or filtering element for the −15 volt power supply which is indicated at 326. A similar capacitor may be used with the +15 volt power supply indicated at 325 if needed. Both the −15 volt and +15 volt power supplies are used only in connection with the amplifiers 314 and 332 in FIG. 3, a separate +5 volt power supply as indicated at 376 is used for the display drivers 306, the transducer 312, and the LED elements of the display segments 308 and 310.

The power supplies 325, 326 and 376 for the apparatus 300 may be embodied in the form of commercially available power supplies operating from a conventional alternating current wall outlet or alternately may be embodied in the form of batteries or other power supply arrangements as are known in the electrical art.

With some rearrangement of the FIG. 3 circuitry, operation of the apparatus 300 from a single power supply or battery could be accomplished. Single battery operation is desirable in fully portable arrangements of the feedback and incentive apparatus in order that patients be free to leave their hospital or treatment room while performing therapy routines. Clearly, such portability can also be arranged with the FIG. 3 illustrated multiple power supplies or other power supply arrangements.

The amplifier 332 in FIG. 3 is connected in the form of a conventional inverting linear amplifier. The voltage gain of this amplifier is determined by the ratio of the resistance selected in the gain control network 342 and the resistor 328 as is known in the electronic art. Disposition of the movable arm in the switch 343 at one of the contacts 344, 346, 348 and 350 of course selects use of one of the gain determining resistors 352, 354, 356 and 358 whose values may be in accordance with the information provided in Table 1. The potentiometer 340 and the two resistors 336 and 338 provide zero adjustment. The resistor 330 in the FIG. 3 circuitry serves as a ground path for the positive input terminal of the inverting amplifier 332 and is selected to have the same 10 kiloohm value as the gain related resistor 328 in accordance with the amplifier manufacturer's instructions.

Since the amplifier 314 is arranged to provide negative excursion output signals and the amplifier 332 is connected as an inverting circuit, the signal applied to the display drivers 304 and 306 has positive excursions as are desired for use of the Table 1 indicated driver circuit embodiments. In fact, the output of the amplifier 332 is preferably arranged to be between 0 and +5 volts and the display driver 362 is arranged to respond to the first half or the first 2½ volts of this signal excursion, while the display driver 360 is arranged to display to the last half or the +2.5 to +5 volt portion of this excursion.

These responses of the display driver circuits 360 and 362 are accomplished by the resistors 366 and 368 which together with the disclosed driver circuit pin connections determine analog-to-digital threshold level setting of internal comparator circuits in the drivers 360 and 362. Use of the reference output signal from the driver 360 in operating both the reference voltage source and the low end of the internal divider resistor network for the driver 362 is notable in this threshold setting arrangement. Additional details regarding the driver circuits 360 and 362 may be understood from the manufacturer's data and application guide information for the embodiments of these circuits indicated in Table 1 herein. The manufacturer's information for all of: the drivers 360 and 362, plus the amplifiers 314 and 332, and the display segments 308 and 310 are hereby incorporated by reference herein.

The resistors 366 in the FIG. 3 apparatus also serve as brightness controls for the LED display and the resistor 372 is used in the driver 360 mode selection circuitry to enable the FIG. 3 illustrated ganged or tandem connection of the two drivers 360 and 362 in accordance with the above-incorporated manufacturer's application data. The switches 364 and 370 provide an election between a bar graph format for the graphic display 216 in FIG. 2 or alternately, for a single dot format of the achieved suction level. For most purposes, use of the bar graph positioning of the switches 364 and 370 is to be preferred. Additional details regarding the selection accomplished by the switches 364 and 370 are also available from the display driver manufacturer's data sheet. The first or lower ordered ten-bit segment 310 of the display are preferably arranged to be green in color and the upper ten bits 308 to be red. This color significance is a matter of choice in arranging the FIGS. 2 and 3 apparatus.

The suction pressure indicating portion of the present invention as disclosed in FIGS. 2 and 3 of the drawings may also be employed in research studies and with patients having speech difficulty or difficulty achieving effective lip movement, patients such as partially paralyzed stroke patients or pediatric patients having developmental disorders or patients having surgical impairment of facial nerves as may occur in certain head and neck cancer surgeries, for example. By way of the FIG. 2 and FIG. 3 apparatus, patients of this type are provided with an effective measurement of the achieved lip seal and thereby a measurement of muscular and neural function in the mouth attended areas of the face.

As arranged in the FIG. 3 electrical schematic, the display segments 308 and 310 provide a real-time or transient indication of the suction level achieved by the using patient, that is the LED displayed image represents instantaneous changes in the achieved oral; sucking act pressure. If desired, this real-time representation may be changed to a remembered, or average, or achieved peak type of display with the use of electrical signal storage apparatus in the FIG. 3 circuit. One arrangement for accomplishing this in analog form is to store the output level of one of the amplifiers 314 and 332 using a storage capacitor and isolating diode therefor these additional elements being connected between the amplifier's output terminal and the succeeding circuit. Discharge of this storage capacitor may be accomplished automatically over a period of time by a shunting resistance or may be achieved with a shunting crowbar circuit as is known in the electrical art.

The present invention is therefore directed to the assisting of surgical, disease, and stroke dysphagia patients, including patients having severe and possibly permanent swallowing impairment. The herein described rehabilitation has in the instance of some total pharyngectomy patients, enabled aspiration-free swallowing in a period of 5 weeks in lieu of the 7 months or never returning to swallowing that is normal for such patients.

While the apparatus and method herein described constitute a preferred embodiment of the invention, it is to be understood that the invention is not limited to this precise form of apparatus or method and that changes may be made therein without departing from the scope of the invention which is defined in the appended claims.

TABLE I

FIG. 2 and 3 Component Parts

| Part Name | Number ID | Value/Source |
|---|---|---|
| Mouthpiece | 202 | NSN 6515LI00833 or United Medical #5904 |
| Filter | 204 | Respigard-2 Bacteria/Viral Markwest Model MQ354 |
| Flexible Tubing | 206 | LVT 102, Stockhouse inc., Riverside, CA |
| Assembly | 208 | 8 × 6 × 4 inches, 2.5 lbs. |
| LED segment (green) | 308 | MV 57164, ECG, Sylvania |
| LED segment (red) | 310 | MV 57164 |
| Transducer | 312 | Cobe disposable |
| Amplifier | 314 | AD 521 by Analog Devices of Norwood, MA |

TABLE I-continued

| FIG. 2 and 3 Component Parts | | |
|---|---|---|
| Part Name | Number ID | Value/Source |
| Resistor | 316 | 100 ohms* |
| Potentiometer | 317, 319 | 20K trimmer |
| Resistor | 320 | 91K* |
| Capacitor | 322, 373 | 0.1 μf, 16 volts |
| +5 volt power supply | 325 | Kepco, Lamda, etc. |
| −15 volt power supply | 326 | Kepco, Lamda, etc. |
| Resistor | 328, 330 | 10K* |
| Amplifier | 332 | OP 27 by PMI (Precision Monolithics Inc. of Santa Clara, CA |
| Resistor | 336, 338 | 4.7K* |
| Potentiometer | 340 | 1K trimmer |
| Display Driver | 360, 362 | LM 3914 by National Semi-conductor Corp. of Santa Clara, CA |
| Resistor | 366 | 12K* |
| Resistor | 368 | 3.9K* |
| +5 volt Power Supply | 376 | Kepco, Lamda, etc. |

*All Resistors are ¼ watt, 2%.

What is claimed is:

1. The dysphagia therapy method for improving the swallow function of a surgical, neurological disease, neuromuscular disease or the like dysphagia patient comprising the steps of:

inducing said patient to repeatedly execute an oral sucking act in a static regimen of dysphagia therapy;

said oral sucking act including static reconditioning exercising usage of tongue, base of tongue, pharynx and related anatomical parts by said patient;

generating an electrical signal representing a mouth cavity oral sucking act suction pressure, below atmospheric pressure, achieved by said patient during said oral sucking act; and rewarding and stimulating said patient into repeated and normalcy-approaching continuing performance of said sucking act dysphagia therapy;

said rewarding and stimulating comprising displaying a graphic representation of said suction pressure electrical signal as a results feedback incentive to said patient.

2. The method of claim 1 wherein said electrical signal comprises electrical representations of instantaneous pressure changes in said patient's mouth cavity.

3. The method of claim 2 wherein said displaying comprises a real-time energization of binary luminous energy emitting elements having predetermined physical array pattern disposition.

4. The method of claim 3 wherein said predetermined physical array pattern comprises a straight line bar graph-like pattern.

5. The method of claim 2 wherein said oral sucking act is executed against a transducer inclusive closed pneumatic circuit.

6. The method of claim 1 wherein said rewarding, stimulating and displaying steps include altering the suction pressure sensitivity of said displaying step in accommodation of increasing oral sucking ability of said patient.

7. The method of claim 1 wherein said generating step includes communicating said mouth cavity suction pressure to a negative pressure to electrical signal transducer element via a patient received mouthpiece.

8. The method for rehabilitating a dysphagic patient comprising the steps of:

motivating said patient to repeatedly execute a static oral sucking act with his/her maximum presently achievable intensity and duration; and providing an oral sucking act responsive and energy flow-communicated sensory stimulation results feedback of selectable and oral sucking-act-compatible pressure ranging to said patient.

9. The method of dysphagia patient therapy comprising the steps of:

establishing a constant volume pneumatically sealed communication path connecting the mouth cavity of said patient and a negative pressure to electrical signal transducer apparatus;

causing said patient to execute and hold a tongue-accomplished, negative pressure generating, static oral sucking act;

communicating said negative pressure via said constant volume pneumatically sealed communication path to said electrical transducer apparatus;

informing said patient, by way of an electrically energized graphical signal representation, of a negative pressure induced electrical signal magnitude generated by said transducer apparatus in response to said static oral sucking act; and encouraging said patient to increase achieved magnitude and time duration of said static oral sucking act negative pressures during a therapy regimen of repeated attempts.

10. The method of claim 9 wherein said electrical transducer apparatus and said graphical signal representation each have a negative pressure range extending between mercury column lengths of zero and two hundred forty millimeters.

11. The method of claim 10 wherein said graphical signal representation range comprises a plurality of patient selectable pressure ranges.

12. The method of claim 9 wherein said establishing step includes disposing said transducer in a location removed from but adjacent said patient and wherein said communication path includes a length of flexible tubing extending between said patient and said transducer location.

13. The method of claim 9 wherein said informing step includes energizing a static negative pressure magnitude-determined number of light emitting diode elements in an array of such elements.

14. The method of claim 13 wherein said informing step includes a timed duration remembering of said generated negative pressure and coincident energizing of said light emitting diode elements.

15. Dysphagia rehabilitation apparatus comprising the combination of:

transducer means including a negative pressure to electrical signal transducer element disposable in pressurized constant volume communication with the mouth cavity of a dysphagia treatment patient for generating an electrical signal representative of oral sucking act related negative pressures generated in said dysphagia patient mouth cavity;

said oral sucking act related negative pressures exceeding human lung capacity negative pressures and extending up to a pressure of two hundred forty millimeters of mercury;

electrical circuit means connected with said transducer element electrical signal for generating a processed electrical signal also representative of said oral sucking act related negative pressures generated in said dysphagia patient mouth cavity; and electrical display means connected with said processed electrical signal for communicating a sucking act negative pressure determined graphic display image feedback incentive to said dysphagia patient.

16. The rehabilitation apparatus of claim 15 wherein said electrical circuit means includes an electronic amplifier circuit.

17. The rehabilitation apparatus of claim 16 wherein said electronic amplifier circuit includes incrementally adjustable gain selection means for selecting between a plurality of predetermined relationships between said sucking act negative pressures and full scale indications on said electrical display means and said indications are indicated as full scale indications on said electrical display means during successive steps of said gain selection means.

18. The rehabilitation apparatus of claim 17 wherein said oral sucking act full scale indications are in response to pressures of 30, 60, 120, and 240 millimeters of mercury below atmospheric pressure.

19. The rehabilitation apparatus of claim 15 wherein said transducer means includes a mouthpiece element receivable in sealed relationship with lip and mouth appendages of said patient.

20. The rehabilitation apparatus of claim 15 wherein said electrical display means includes a linearly disposed array of light contrast elements and electrical circuit means for energizing successive of said light contrast elements in response to an increasing amplitude of said processed electrical signal.

21. The rehabilitation apparatus of claim 20 wherein said electrical display means also includes circuit means for energizing said light contrast elements in an nth, (n+1)th, (n+2)th, (n+3)th and so on element sequence up to an amplitude determined final element in response to an increasing sucking act related negative pressure and increasing amplitude of said processed electrical signal and further includes electrical circuit means for cumulative energization of all of said light emitting elements up to said selected final element in each said sequence in a bar graph-like display configuration.

22. The apparatus of claim 21 wherein said light contrast elements comprise light emitting diodes.

23. Electrical apparatus for assisting rehabilitation of a dysphagia patient comprising the combination of:

electrical signal generating means for constant volume measurement of transient mouth pressure, below atmospheric pressure and below breathing generatable pressure, achieved during oral sucking act therapy performed by said patient; and electrical display means responsive to said electrical signal generating means for communicating a remembered and stable sensory stimulus incentive feedback signal responsive to said measured mouth pressure to said patient.

* * * * *